United States Patent
Stanat et al.

(10) Patent No.: US 7,425,662 B2
(45) Date of Patent: Sep. 16, 2008

(54) OLIGOMERIZATION OF OLEFINS

(75) Inventors: Jon E. Stanat, Baton Rouge, LA (US); Georges M. K. Mathys, Bierbeek (BE); David Wayne Turner, Raymond, ME (US); Jane C. Cheng, Bridgewater, NJ (US); Stephen W. Beadle, Prairieville, LA (US); Cesar M. Cheng Guajardo, Baton Rouge, LA (US); Roger Eijkhoudt, Breda (NL); Allen D. Godwin, Seabrook, TX (US); Ernest E. Green, Baton Rouge, LA (US); Charles M. Yarbrough, Baton Rouge, LA (US); Raphael Frans Caers, Edegem (BE); Carolyn B. Duncan, Franklin, GA (US); Ramzi Y. Saleh, Baton Rouge, LA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 425 days.

(21) Appl. No.: 10/509,356

(22) PCT Filed: Mar. 28, 2003

(86) PCT No.: PCT/US03/09591

§ 371 (c)(1), (2), (4) Date: Sep. 28, 2004

(87) PCT Pub. No.: WO03/082780

PCT Pub. Date: Oct. 9, 2003

(65) Prior Publication Data

US 2005/0182284 A1    Aug. 18, 2005

Related U.S. Application Data

(60) Provisional application No. 60/369,233, filed on Mar. 29, 2002, provisional application No. 60/369,235, filed on Mar. 29, 2002.

(51) Int. Cl.
$C07C\ 2/20$ (2006.01)

(52) U.S. Cl. ............... 585/533; 585/520

(58) Field of Classification Search ............... 585/520, 585/533
See application file for complete search history.

(56) References Cited

U.S. PATENT DOCUMENTS

| | | | | |
|---|---|---|---|---|
| 4,855,528 | A | 8/1989 | Young et al. | 585/531 |
| 4,973,788 | A | 11/1990 | Lin et al. | 585/511 |
| 5,026,933 | A | 6/1991 | Blain et al. | 585/7 |
| 5,113,030 | A | 5/1992 | Chen et al. | 585/10 |
| 5,210,347 | A | 5/1993 | Chen et al. | 585/14 |
| 5,284,989 | A | 2/1994 | Apelian et al. | 585/533 |

(Continued)

FOREIGN PATENT DOCUMENTS

EP    0 402 051 A2 * 12/1990

(Continued)

Primary Examiner—Glenn Caldarola
Assistant Examiner—In Suk Bullock
(74) Attorney, Agent, or Firm—Andrew B. Griffis

(57) ABSTRACT

A selectivated molecular sieve, e.g., ZSM-22 or ZSM-23, is used as olefin oligomerization catalyst to provide product, e.g., octenes and dodecenes from butene, having a low degree of branching and hindered double bonds.

1 Claim, 5 Drawing Sheets

U.S. PATENT DOCUMENTS

| | | | |
|---|---|---|---|
| 5,554,310 A | 9/1996 | Rossi et al. | 508/591 |
| 6,013,851 A | 1/2000 | Verrelst et al. | 585/533 |
| 2002/0111523 A1 | 8/2002 | Mathys et al. | 585/518 |

FOREIGN PATENT DOCUMENTS

| | | |
|---|---|---|
| WO | WO 96/22264 | 7/1996 |
| WO | WO 97/38957 | 10/1997 |
| WO | WO 99/05241 | 2/1999 |
| WO | WO 02/060842 A1 | 8/2002 |

* cited by examiner

OLIGOMERIZATION OF OLEFINS

This application is a National Stage Application of International Application No. PCT/US03/09591, filed Mar. 28, 2003, which claims the benefit of Provisional Application No. 60/369,233, filed Mar. 29, 2002 and Provisional Application No. 60/369,235, filed Mar. 29, 2002. These applications are hereby incorporated by reference.

FIELD OF THE INVENTION

This invention relates to a process for the manufacture of higher molecular weight organic species from lower molecular weight materials, especially olefins, more especially alkenes, by a process including an oligomerization step. The invention also relates to the oligomers produced, their use as feedstocks for further reactions, the products of those further reactions, and compositions containing them.

BACKGROUND OF THE INVENTION

The products of olefin oligomerization are usually mixtures of, for example, olefin dimers, trimers, and higher oligomers. Further, each olefin oligomer is itself usually a mixture of isomers, both skeletal and in double bond location. Highly branched isomers are less reactive than linear or lightly branched materials in many of the downstream reactions for which the oligomers are used as feedstocks. This is also true of isomers in which access to the double bond is sterically hindered. In this specification, the olefin types of the oligomers are denominated according to the degree of substitution of the double bond, as follows:

| | |
|---|---|
| Type I: | R—CH=$CH_2$, mono-substituted |
| Type II: | R—CH=CH—R, disubstituted |
| Type III: | RRC=$CH_2$, disubstituted |
| Type IV: | RRC=CHR, trisubstituted |
| Type V: | RRC=CRR, tetrasubstituted | wherein R represents an alkyl group, each R being the same or different. Type I compounds are sometimes described as α- or vinyl olefins and Type III as vinylidene olefins. Type IV is sometimes subdivided to provide a Type IVA, in which access to the double bond is less hindered, and Type IVB where it is more hindered.

The degree of branching and double bond Type distribution affect some properties and performance of the olefin derivatives, e.g., the low temperature performance and volatility when converted to alcohols and subsequently to plasticizers.

The degree of branching and mixture of double bond types also affect the reactivity of the oligomer olefins to alkylation and, especially, oxonation. Types I and II have excellent reactivity, Type III fair reactivity, Type IVA good reactivity, and types IVB and V poor reactivity. In alkylation, reactivity is effected by the ease of protonation of the more readily approached, less hindered, double bonds of the preferred structures. Similar effects apply to the reactivity of the oligomer olefins to oxonation, the low branching and less hindered double bonds allowing the molecules to be converted to aldehydes and alcohols rather than being hydrogenated to paraffins.

Furthermore, detergent products obtainable from the products of alkylation of the olefinic oligomer products, especially those having 10 or more carbon atoms, having low Type IVB and V contents and low degrees of branching, would have numerous advantages in use. These include better hard water solubility, and better biodegradability resulting from the lower levels of quaternary carbons.

As examples of the alkylarenes resulting from reaction of oligomer olefins with arenes there may be mentioned the alkyltoluenes, alkylnaphthalenes and, more especially, the alkylbenzenes. Processes for forming these products from arenes and olefins are known per se, and need not be detailed further here. Such alkylarenes are intermediates in the production of advantageous alkylarene sulfonic acids and, after neutralization, of alkylarene sulfonates, also by processes known per se.

There is accordingly a continuing need for olefin oligomerization processes that yield products of a low degree of branching and a low proportion of Type V materials. Advantageously, the products desirably also have, in addition to a low degree of branching, a high proportion of isomers with a single branch which branch is a lower alkyl, i.e., $C_1$ to $C_3$, especially a methyl, branch.

It has been proposed to use as starting materials for oligomerization propylene-rich feedstocks. Such feedstocks tend to yield product with a high proportion of highly branched isomers. Moreover, such feedstocks are becoming increasingly scarce and expensive, and there is therefore also a need to provide oligomerization processes that produce products meeting the above-mentioned requirements from more readily available and less costly feedstocks.

Numerous catalyst systems have been proposed for olefin oligomerization processes. Solid phosphoric acid, nickel- and cobalt-based systems, and acidic crystalline molecular sieves have all been used.

SUMMARY OF THE INVENTION

It has been observed that in crystalline molecular sieve-catalysed oligomerization, the extent of branching in the product is dependent, inter alia, on the pore architecture of the crystalline molecular sieve used and, for a given crystalline molecular sieve, on its particle size and pre-treatment, if any. (In the remainder of this description, crystalline molecular sieves will for brevity sometimes be referred to as zeolites. It will, however, be appreciated that the silicon and aluminum components present in true zeolites may be supplemented and/or replaced by other elements, and the term is used herein, and is to be interpreted, broadly.) It is believed that one type of reaction which takes place at the acid sites within the channels or pores produces predominantly linear or lightly branched products, while a second type takes place on the outer surface, producing more highly branched products. Clearly, using larger particle size zeolites will favor the former reaction, but smaller particle size catalysts are preferred for kinetic, and hence economic, reasons. It has been found that enhanced linearity results from using as catalyst a medium pore zeolite having selectively deactivated surface acid sites, a procedure hereinafter referred to as "selectivation".

The present invention accordingly provides a process for the oligomerization of olefins, which process comprises the steps of contacting an olefinic feedstock containing at least one olefin having 4 or 5 carbon atoms under oligomerization conditions with a selectivated crystalline molecular sieve oligomerization catalyst and recovering an olefinic oligomeric product, of which at least a dimeric or a trimeric component has, and preferably both such components have, an average degree of branching of at most 2.0 and a Type V double bond content of at most 10%. More especially, average degrees of branching are in the range of from 0.5 to 2.0, preferably from 0.8 to 2.0, and more preferably from 1.0 to 1.5.

Advantageously the oligomer product from butene comprises octenes with at least about 0.8, more generally at least about 0.9, to at most about 1.3, preferably at most about 1.1, lower alkyl, especially methyl, branches, dodecenes with about 1.05 to at most about 1.6, preferably at most about 1.4, lower alkyl, especially methyl, branches, and hexadecenes with at least about 1.05, more generally at least about 1.10, to at most about 1.7, preferably at most about 1.6, lower alkyl, especially methyl, branches.

Advantageously, the proportion of the dimer product that is linear or has single methyl group branching is at least 62%, preferably from 62 to 83%.

Advantageously, the dimer, especially the octene, component has an average degree of branching of at most 2.0, and a skeletal isomer content:

| Type I   | from 0.7 to 2.0   |
|----------|-------------------|
| Type II  | from 18.0 to 30.0 |
| Type III | from 5.0 to 10.0  |
| Type IV  | from 45.0 to 65.0 |
| Type V   | at most 10%.      |

Advantageously, the trimeric component, especially of butene oligomerization, has a double bond structure as follows:

| Type I    | At least 0.5%, preferably 1 to 10%  |
|-----------|-------------------------------------|
| Type II   | At least 20%, preferably 25 to 45%  |
| Type III  | At least 3.5%, preferably 3.5 to 6% |
| Type IVA  | At least 45%, preferably 45 to 65%  |
| Type IVB  | At most 5%, preferably at most 3%   |
| Type V    | At most 8%, preferably at most 5%   |

More advantageously, the Type V content is at most 2%.

Preferably, the trimeric component has a double bond structure within the following ranges:

| Type I    | At least 0.5, more generally from 1.3 to 2.8 |
|-----------|----------------------------------------------|
| Type II   | 31.6 to 41.7%                                |
| Type III  | 3.8 to 5.2%                                  |
| Type IVA  | 46.2 to 52.9%                                |
| Type IVB  | 0 to 2.2%                                    |
| Type V    | 0 to 1.2%                                    |

Advantageously, the type V content of the tetrameric component, especially of butene oligomerization, is at most 10%, preferably at most 8%, and preferably at most 5%. More generally, since the average branchiness of the product of oligomerization of an olefin of a given carbon number depends on the oligomerization degree (dimer, trimer, etc.), in an additional preferred process of the invention the degree of branching of an oligomeric product is given by $$ABR \leq 1.70 + 1.37(1 - e^{(-0.24(CN/FDCN - 2))})$$

where CN=carbon number of the oligomer product mixture under consideration ABR=average branchiness of the oligomer product mixture with carbon number CN
FDCN=average carbon number of feed olefins Thus, for dimer, the value of average branchiness is advantageously at most 1.7 and for trimer the value is advantageously at most 1.992. Similarly, in an additional preferred process, the mole percentage of Type V material in an oligomeric product is given by $$M5 \leq 8.5 + 35(1 - e^{(-0.5(CN/FDCN - 2))})$$

where M5=mole percentage of Type V in the oligomer product under consideration.

Thus, for dimer, the value of the Type V mole percentage is advantageously at most 8.5 and for trimer the value is advantageously at most 22.3. Advantageously, the product of the additional processes of the invention is one having both the specified branchiness and Type V characteristics.

The feedstock may contain, in addition to $C_4$ and/or $C_5$ olefins, other olefinic components, including ethylene, propene and $C_6$ and higher olefins. The inclusion of such other olefins, especially propene, is of especial advantage when the target product is to include $C_{10}$ oligomers. As $C_4$ olefins there may be mentioned all the butene isomers, preferably the normal butenes. Suitable feeds are made by thermal, steam, or catalytic cracking, or by processes that convert oxygenates to olefins. These $C_4$ streams may be treated for the removal of butadiene and/or where appropriate also for the removal of isobutylene. The butene-containing feed to oligomerization may be dilute, i.e. contain from 20 to 50% by weight of normal butenes, but may also be rich, i.e. contain from 45 to 98% normal butenes. For process control reasons, rich feed streams are optionally diluted by returning part of the unreacted $C_4$ and/or $C_5$ olefins and paraffins separated from the oligomerization product back as feed for the oligomerization reactor section. As a preferred feedstock may be mentioned streams containing, by weight, about 40 to 90% butenes, advantageously about 45 to 80% butenes, preferably 45 to 70% butenes, more preferably about 48 to 65% butenes and most preferably 48 to 57% butenes. A typical feedstock may contain 20 to 24% 1-butene, 17 to 20% trans-2-butene, 11 to 13% cis-2-butene and about 1% isobutylene, and from about 35, preferably from about 40, to about 50% butanes and traces of other light alkanes, alkenes, and ethers. As $C_5$ olefins, there may be mentioned all the pentene isomers. The feedstock may in addition contain inert materials, for example, paraffins, e.g., butanes, either as incidental impurities or as deliberately present diluents. The feedstock may be hydrated or may already contain water or other oxygenate. Depending on the selectivation method, the feedstock may also contain a small proportion of a selectivation agent, to maintain the desired properties of the catalyst throughout the process.

Advantageously, oligomerization is carried out at a temperature within the range of from about 160° C. to about 250° C., especially from 190° C. to 230° C., and more especially from 210° C. to 220° C. Advantageously, pressure is in the range of from about 3.4 MPa to about 10.5 MPa, especially from 5 MPa to 9 MPa, and more especially from 6 to 8 MPa. Advantageously, the weight hourly space velocity (WHSV) based on the olefin in the feed is in the range of from about 0.1 to about 4.0, especially from 1.0 to 3.0, more especially from 1.75 to 2.25. It has been found that branchiness and Type V content of the product increase with the severity of the reaction conditions, severity being represented by a combination of high temperatures and low WHSV. Predominantly temperatures of 260° C. and above and conversion rates of 65% and above are to be avoided.

As selectivated zeolites suitable for use as catalysts in the process of the invention, there may be mentioned, for example, medium pore zeolites, especially one having a small 10 member ring pore structure. Preferred zeolites are ZSM-22 and, more especially, ZSM-23. Selectivation may be effected by treatment of the zeolite by an amine, especially a bulky amine, i.e., one having an effective cross-section greater than that of the zeolite pore size. Examples are dialkyl or, especially, trialkylpyridines. A preferred amine is 2,4,6-trimethylpyridine (collidine). Alternatively, as described in U.S. Pat. No. 6,013,851, the disclosure of which is incorporated herein by reference, a surface layer may be deposited on a catalyst core.

Advantageously, about 10% to about 50%, preferably from 10 to 30%, of acid sites are selectivated. The quantity of base needed to selectivate the desired proportion of acid sites may be determined from the silica-alumina ratio of the zeolites.

Typically, catalyst to be selectivated is dried in an oven at about 95° C. under vacuum and, minimizing exposure to air, transferred to a vessel arranged to be tumbled, e.g., a Rotavapor® apparatus. The calculated quantity of amine necessary to selectivate the desired acid site proportion is dissolved in an inert solvent, e.g., collidine in pentane for ZSM-23, and added to the vessel and tumbled for sufficient time to ensure complete reaction. Subsequently the solvent is removed under vacuum. The selectivated catalyst may then be transferred, without precaution to minimize air contact, to the oligomerization reactor, and heated under nitrogen for sufficient time (e.g., 8 hours at 150° C.) to ensure that the amine has migrated to the most active acid sites.

The oligomerization process is advantageously carried out in a fixed bed or tubular reactor contacting the selectivated zeolite catalyst. If a fixed bed reactor is used, heat of reaction is removed by inter-reactor cooling, or temperature is controlled by cooled recycled materials being returned to the reactor. If a tubular reactor is used, the catalyst may be retained in the tubes of a heat-exchanger, the heat of reaction being transferred through the tube for use in heating or steam generation.

The crude reaction product is advantageously separated by carbon number, for example, by distillation. Optionally, crude product or unreacted feed may be partially returned to the reactor to control carbon number product, or light ends from the separated product recycled to the same end.

The product, or separated components thereof, may then be used as feedstock for numerous purposes. For example, the olefin may be converted to an aldehyde having one more carbon atom than the olefin by oxonation, and the aldehyde oxidized to an acid or, advantageously, hydrogenated to form the corresponding alcohol, which may in turn be esterified.

The low degree of branching and less hindered double bond structure result in improved yields and/or higher conversions in the oxonation process, because these species react quickly to yield aldehydes and alcohols before being hydrogenated to paraffins.

In a typical commercial process for the manufacture of a plasticizer ester, the alcohol is employed in excess over the acid, and alcohol is stripped from the ester product and recycled. In recycling, the less reactive isomers tend to concentrate as the reaction processes, resulting in less efficient production over time. As a result of the greater reactivity of the alcohols resulting from oxonation of the olefin products of the invention, this disadvantage is reduced. Further, the alcohols and resulting esters have a lower volatility and viscosity, and greater biodegradability, than corresponding more highly branched products.

The alcohols may also be used as starting materials in the formation of ethers of commercial importance.

The esters and ethers produced by the process of the invention are suitable for use as solvents, paint coalescers, plasticizers, adhesives, surfactants, viscosity index improvers, synthetic lubricants, flame retardants, lubricant components, anti-wear agents, hydraulic fluids, cetane improvers, drilling fluids, thermoplastic and textile processing aids, polymer, especially vinyl chloride polymer, stabilizers, polymerizable monomers and fragrances.

The acid portion of the ester may be inorganic or organic; if the latter, a carboxylic acid is preferred. Among organic acids, aromatic acids are preferred for plasticizer manufacture, although aliphatic acids are also employed. As examples of acids, acetic, propionic, valeric, isovaleric, n-heptanoic, n-octanoic, n-decanoic, neodecanoic, lauric, stearic, isostearic, oleic, erucic, cyclohexanoic and dioic, succinic, phthalic (1,2-benzenedicarboxylic), isophthalic, terephthalic, adipic, fumaric, azelaic, 2-methylpentanoic, 2,4-dimethylheptanoic, 2,4,6-trimethylnonanoic, sebacic, trimellitic, pyromellitic, acrylic, methacrylic, tall oil, naphthenic and naphthalene-type acids, carbonic, nitric, sulphuric, phosphoric and phosphorous and their thio-analogous, acids and $C_3$ to $C_{13}$ oxo and neo acids generally may be mentioned. The esters of the $C_9$ and especially the $C_{13}$ alcohols with oxo and neo acids have especial utility as drilling fluids and power transmission fluids. The phosphate esters have especial utility as flame retardants while the phosphite esters provide vinyl chloride polymer stabilizers. The esters with unsaturated carboxylic acids, e.g., with acrylic and methacrylic acid, provide polymerizable monomers, suitable as sole or co-monomer in thermoplastics manufacture, or in polymers used in or as adhesives, VI improvers, and coating resins.

Both esters and ethers provide surfactants, for use, for example, in detergents, emulsifiers, and demulsifiers. As specific examples there may more especially be mentioned the following derivatives of the alcohols, ROH:

sulphates, $ROSO_3H$, and their salts, especially sodium;

sulphonates, $RSO_3H$, and their salts, especially sodium;

alkoxy sulphonates, otherwise known as ethersulphates, for example $RO(R^2O)_nSO_3H$, wherein $R^2O$ represents ethylenoxy (EO) or propylenoxy (PO) and n advantageously represents from 1 to 30, preferably from 1 to 4, and their salts, especially sodium;

alkoxylates, for example, those containing EO, or PO, or both groups, for example, polyethyleneglycol ethers RO(EO)mH with m being, for example, from 3 to 100, more especially from 3 to 15, or poly-polyglycol ethers, RO(EO)p(PO)qH or RO(PO)q(EO)pH wherein p advantageously represents from 3 to 6 and q advantageously independently represents from 3 to 6; and etheramines, for example, oxyalkylene amines, for example the compounds of the formula ROR3NH2 or ROR4NHR5NH2 wherein R3, R4 and R5 each independently represent an alkylene group, advantageously ethylene or propylene, for example the oxypropylene amine RO(CH2)3NH2, diamines RO(CH2)2NH(CH2)2NH2, and their nitriles (—C☐N), alkoxylates (e.g., —N(C2H4OH)2 or —N(C3H6OH)2 or quaternary ammonium salts, for example, —N(EO or PO)2CH3]+X—, where X may represent, for example, chlorine, of the mono- or diamines.

The glycidyl ether, $ROCH_2CH$—$CH_2$ has utility in the manufacture of coating resins.

Specific examples of esters produced in accordance with the invention and their applications include the esters with acetic (solvent), acrylic and methacrylic (polymerizable monomer), phthalic, adipic, sebacic, trimellitic and pyromellitic acids (plasticizer, lubricant or lubricant component for, e.g., engine oil, hydraulic fluid, refrigerant oil for hydrofluorocarbon refrigerants, fuel additive for mogas and diesel fuels).

The invention also provides a dihydrocarbyl dithiophosphoric acid of the alcohols produced by the invention and their metal salts, especially those from the dimer. Advantageously, the metal is zinc. The DDPA's and DDP's are made by methods known per se.

The invention further provides a composition comprising a plasticizer ester, or plasticizer composition, especially those from the dimer, but also those from the trimer, made according to the invention and a polymer plasticized thereby. The invention also provides a shaped structure formed of the plasticized polymer.

The esters produced according to the invention may be used as a plasticizer for numerous polymers, for example, cellulose acetate; homo- and copolymers of aromatic vinyl compounds e.g., styrene, or of vinyl esters with carboxylic acids e.g., ethylene/vinyl acetate copolymers; halogen-containing polymers, especially vinyl chloride homo- and copolymers, more especially those copolymers with vinyl esters of carboxylic acids, esters of unsaturated carboxylic acids e.g., methacrylates, and/or olefins; nitrile rubbers; and post-chlorinated vinyl chloride polymers. Poly(vinyl chloride) is of especial interest.

The plasticizer esters produced by the invention result in plasticized products of greater low temperature flexibility, better UV stability and longer product life.

The proportion of plasticizer may vary within wide limits, but is generally 10 to 200 parts by weight per 100 parts of polymer, more especially 20 to 100 parts per 100.

The esters produced by the invention may be used alone as plasticizer, or in admixture with one another, or in admixture with other plasticizers, for example, dibutyl, dipentyl, dihexyl, diheptyl, dioctyl, dinonyl, didecyl, diundecyl, didodecyl, ditridecyl phthalates, cyclohexanoates, cyclohexanedioates, trimellitates or adipates, or butyl benzyl phthalate, or mixtures thereof. They may also or instead be used with a secondary plasticizer, e.g., a chlorinated paraffin, Texanol isobutyrate, or a processing oil. If used in admixture, it is the total proportion of plasticizer that is advantageously within the ranges given above.

The plasticized polymeric compositions of the invention may be made up in numerous forms and have various end-uses. These include flooring materials, wall coverings, moulded products, upholstery materials, leather substitutes, electrical insulation, especially wire and cable, coated fabrics, shoes, toys, and automobile parts. For example, they may be in the form of a dryblend, a paste, or a plastisol, depending on the grade of the resin employed.

Dryblends made using the less highly branched esters made according to the invention will dryblend faster than those made using more highly branched esters of the same carbon number, affording higher throughput. Emissions during processing will be lower, and melt viscosity will be reduced. The low temperature properties and outdoor aging of the product will be improved.

Dryblends may be processed by hot melt compounding and further processed into finished flexible products, e.g., film, by calendering, electrical insulation, e.g., by extrusion, and shoes, toys, and other molded products by, e.g., injection molding. For shoes, the improved flexibility resulting from the use of the less highly branched esters improves flexibility and hence give longer life. Alternatively, for a given degree of flexibility, the greater efficiency of the less highly branched esters enables less plasticizer to be used, reducing costs when compared on a weight basis.

Plastisols made using the esters have lower viscosity, lessening the need for viscosity control agents. They may be used, for example, as coatings, in dipping, spraying, injection or rotational moulding, extrusion, or as self-supporting films and sheets, and may readily be foamed.

The invention also provides the acids derived from the olefin oligomers, their esters, e.g., polyol esters, mono esters, glycidyl esters, vinyl esters and metal salts.

The invention also provides a composition comprising an ester produced by the invention and a refrigerant, especially a fluorocarbon refrigerant, and more especially HFC 32 (difluoromethane) or HFC 134a (1,1,1,2-tetrafluoroethane). More especially, the invention provides such a composition also comprising at least one of a hydrolytic stability enhancer, e.g., a hindered phenol or an aromatic amine, an antioxidant, corrosion inhibitor, and a metal deactivator.

Esters, especially those from the trimer, with monobasic and dibasic acids are preferred for lubricants and lubricant components; advantageously the resulting esters contain from 15 to 40 carbon atoms; adipates, azelates, and phthalates are especially preferred for lubricant manufacture. The lower viscosities and lower volatilities resulting from the use of the esters produced according to the invention give especial advantage in the lubricant field.

A particularly preferred ester obtainable by the process of the invention is the ditridecyl adipate resulting from oxonation and hydrogenation of the $C_{12}$ oligomer product and subsequent esterification of the alcohol with adipic acid. $C_{13}$ alcohols made by prior art processes, for example solid phosphoric acid catalysed oligomerization, are highly branched, and variable in branchiness, as a result of which they are poorly biodegradable. The lubricant industry has a need for lubricant basestocks that are more readily biodegradable, and the reduced branchiness, for example about 1.3 methyl groups per molecule, of the product according to the invention enables it to meet the industry's needs, facilitating the provision of biodegradable lubricants containing modern additive packages.

More especially, however, as indicated above, the oligomeric olefins produced by the process of the invention have especial utility in the manufacture of surfactants, especially detergents, having valuable advantages, including hard water solubility and biodegradability. The present invention accordingly further provides a process in which the oligomeric olefinic product and an arene are reacted, advantageously in the presence of an alkylation catalyst, and recovering an alkylarene. If desired or required, before the alkylation step, the olefinic oligomerization product may be treated to recover a $C_{10}+$ fraction, or if desired a $C_{12}+$ fraction, and that fraction and the arene are reacted. Advantageously the arene is toluene, naphthalene or, especially, benzene.

Further, the invention provides a process for the manufacture of an alkylaryl sulfonic acid in which the alkylarene produced by the above process of the invention is treated with a sulfonating agent. As suitable sulfonating agents there may be mentioned, for example, chlorosulfonic acid. If desired, before sulfonation, the alkylarene may be alkoxylated, especially ethoxylated.

Still further, the invention provides a process for the manufacture of an alkylsulfonate in which the sulfonic acid produced by the above process is converted to a sulfonate, for example by treatment with a base, for example ammonium hydroxide or an alkali metal-derived base, e.g., sodium hydroxide or methoxide.

Alternatively, the olefin oligomers may be converted directly into surfactants by sulfonation, for example by reaction with sulfur trioxide, or converted to sulfate or phosphate surfactants by reaction with sulfonic or phosphoric acid.

Further, the olefin oligomers may be converted by Reppe or Koch chemistry into acids, which if desired may be alkoxylated, especially ethoxylated. Reaction with ethylene oxide in particular with Reppe acids yields ethers suitable for use in low sudsing detergents for automatic washers, e.g., by the reaction $$RCOOH + n+1(CH_2)_2O \rightarrow RCOO(CH_2CH_2O)_n CH_2CH_2OH$$

Similarly, cationic detergents may be made by reaction of the Reppe acids with various amines.

The invention also provides the acids derived from the olefin oligomers, their esters, e.g., polyol esters, mono esters, glycidyl esters, vinyl esters and metal salts.

BRIEF DESCRIPTION OF THE DRAWINGS

Certain aspects of the invention will now be described by way of example only with reference to the accompanying drawings, in which:

Referring to FIG. 1, a $C_4$, $C_5$, or mixed olefin feed containing at least one of $C_4$ and $C_5$ olefins 1 is fed in via heat-exchangers 2 to reactors 3a, 3b, in parallel and subsequently to reactors 4,5 in series. The product from reactor 5 is fed to the product recovery tower 8 via selectivation agent removal unit 6 and de-butanizer tower 7. $C_8$ dimer (from butene) is taken off as overhead, with optional recycle via line 9 to reactors 3a and 3b if the $C_{12}+$ product is to be maximized. The de-butanizer tower overheads may optionally be recycled to the reactors 3a and 3b via line 10.

FIG. 2 shows a comparison of the branching index of octene products produced according to the invention, using selectivated ZSM-22 or, preferably, ZSM-23, compared with that of the prior art catalysts, normal ZSM-22 and ZSM-57, and solid phosphoric acid.

FIG. 3 shows the improvement in aldehyde yield when oxonating octenes produced according to the invention using sufficiently selectivated ZSM-23 catalyst compared with the results obtained when using octenes obtained by inadequately selectivated ZSM-23 or solid phosphoric acid. In all cases, oxonation was carried out using cobalt-based catalyst.

Referring now to FIG. 4, a $C_4$, $C_5$, or mixed olefin feed containing at least one of $C_4$ and $C_5$ olefins 11 is fed in via heat-exchangers 12 to reactors 13a, 13b, in parallel and subsequently to reactors 14,15 in series. The product from reactor 15 is fed to the $C_8$ product recovery tower 18 via selectivation agent removal unit 16 and de-butanizer tower 17. $C_8$ dimer (from butene) is taken off from tower 18 as overhead, with optional recycle via line 19 to reactors 13a and 13b if the $C_{12}+$ product is to be maximized. The de-butanizer tower overheads may optionally be recycled to the reactors 13a and 13b via line 20.

The bottoms product from tower 18 is fed to the $C_{12}$ product recovery tower 21, $C_{12}$ product being taken off as overhead, with optional recycle via line 22 if the $C_{16}+$ product is to be maximized. The bottoms product from tower 21 is fed to product recovery tower 23, where $C_{12}$ to $C_{16}$ product is taken off as overheads with $C_{16}$ to $C_{20}$ product being taken off as bottoms product.

Figure 1:
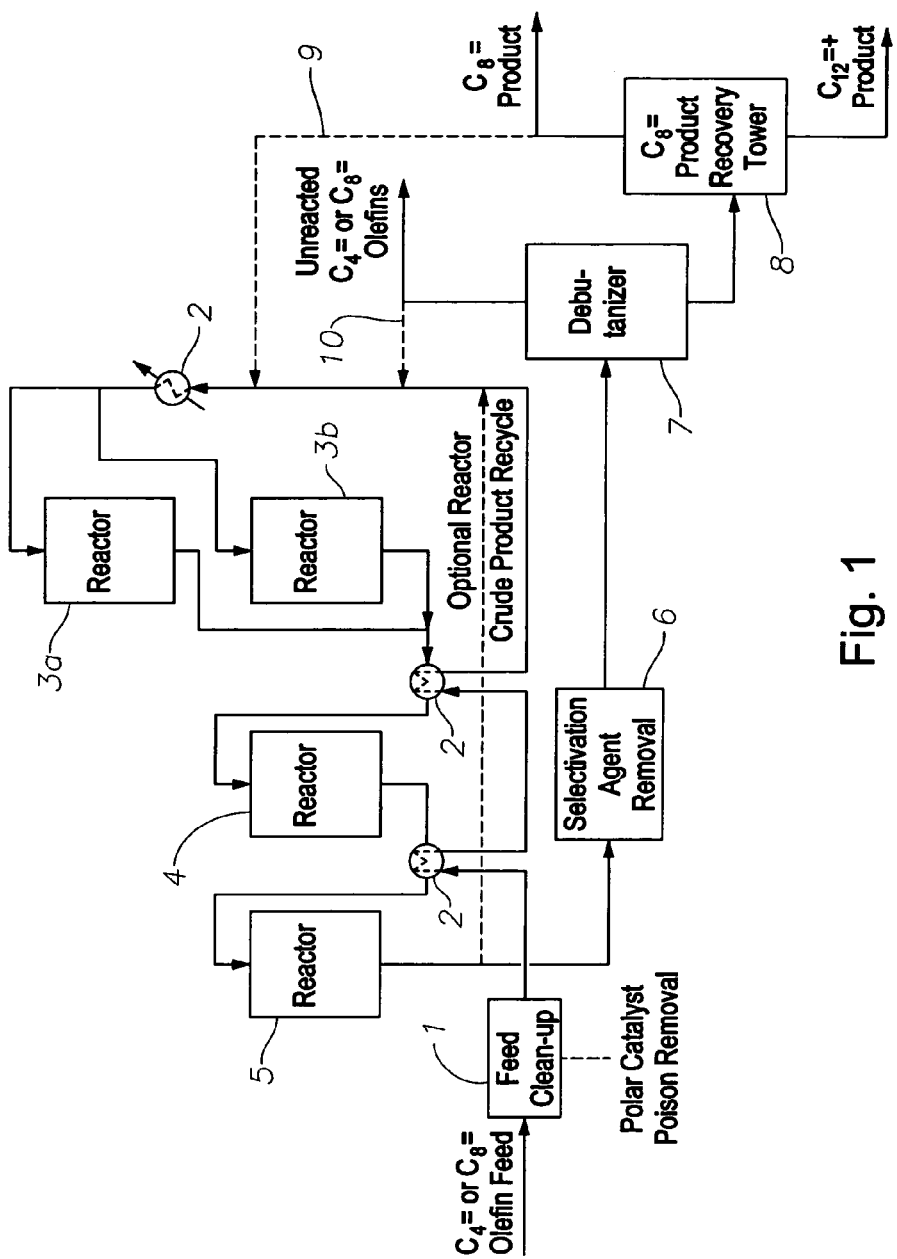
FIG. 1 is a flow diagram of a process of oligomerization, predominantly directed to production and recovery of a dimer product.
Figure 2:
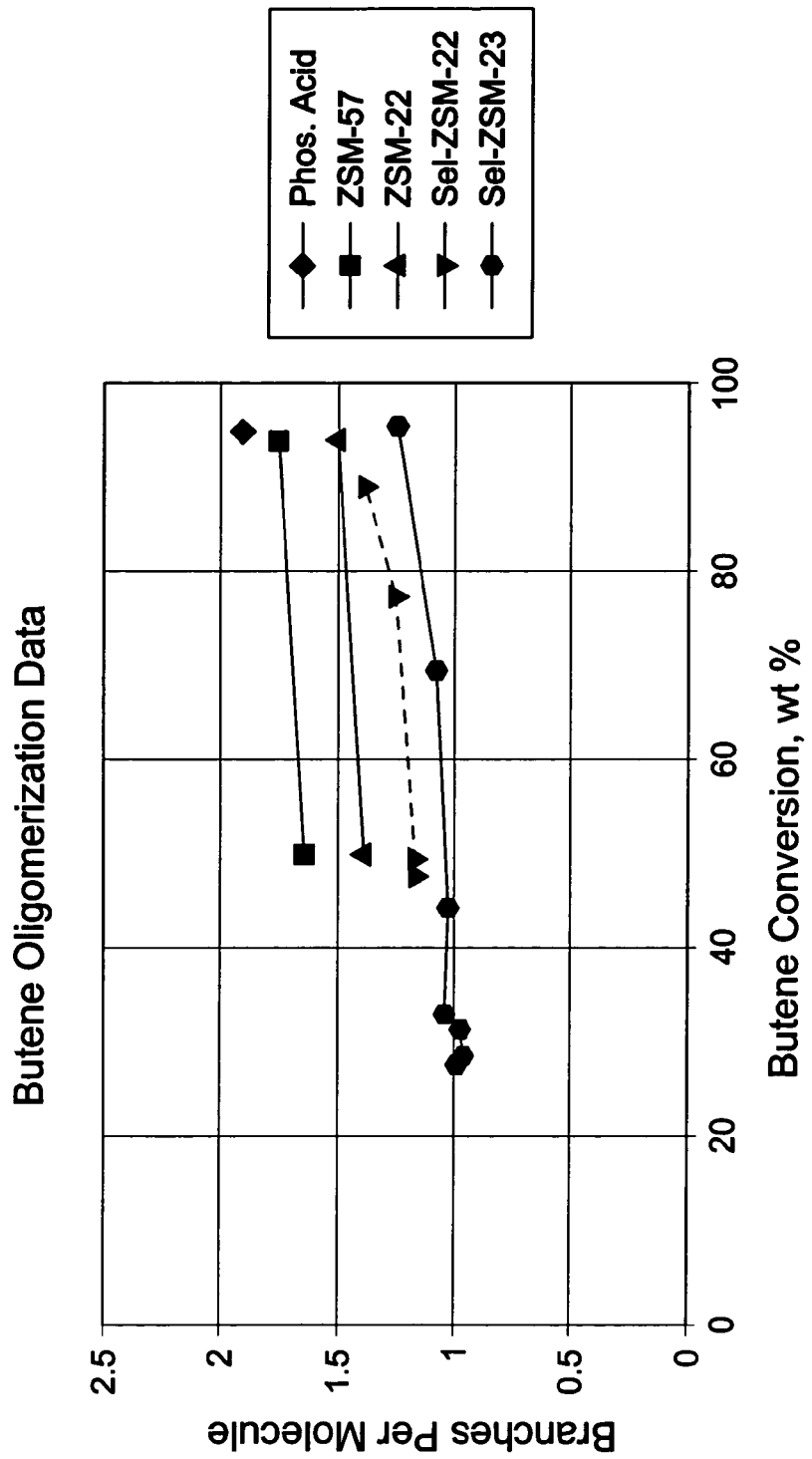
FIG. 2 is a graph showing the variation of octene branchiness with conversion for $C_4$ to $C_8$ oligomerization.
Figure 3:
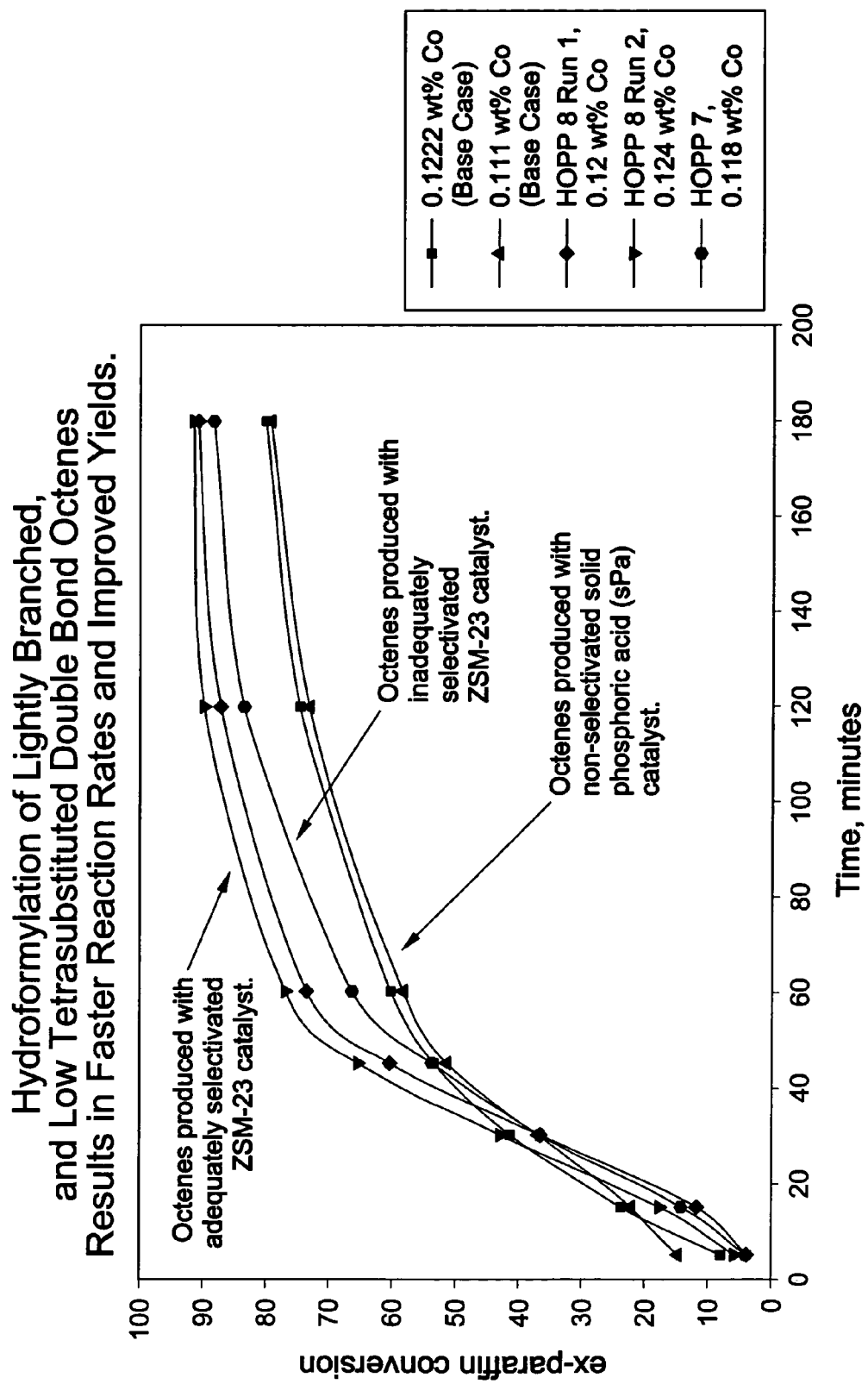
FIG. 3 is a graph showing the improved yields of aldehyde available when oxonating the octenes produced by the process of the invention.
Figure 4:
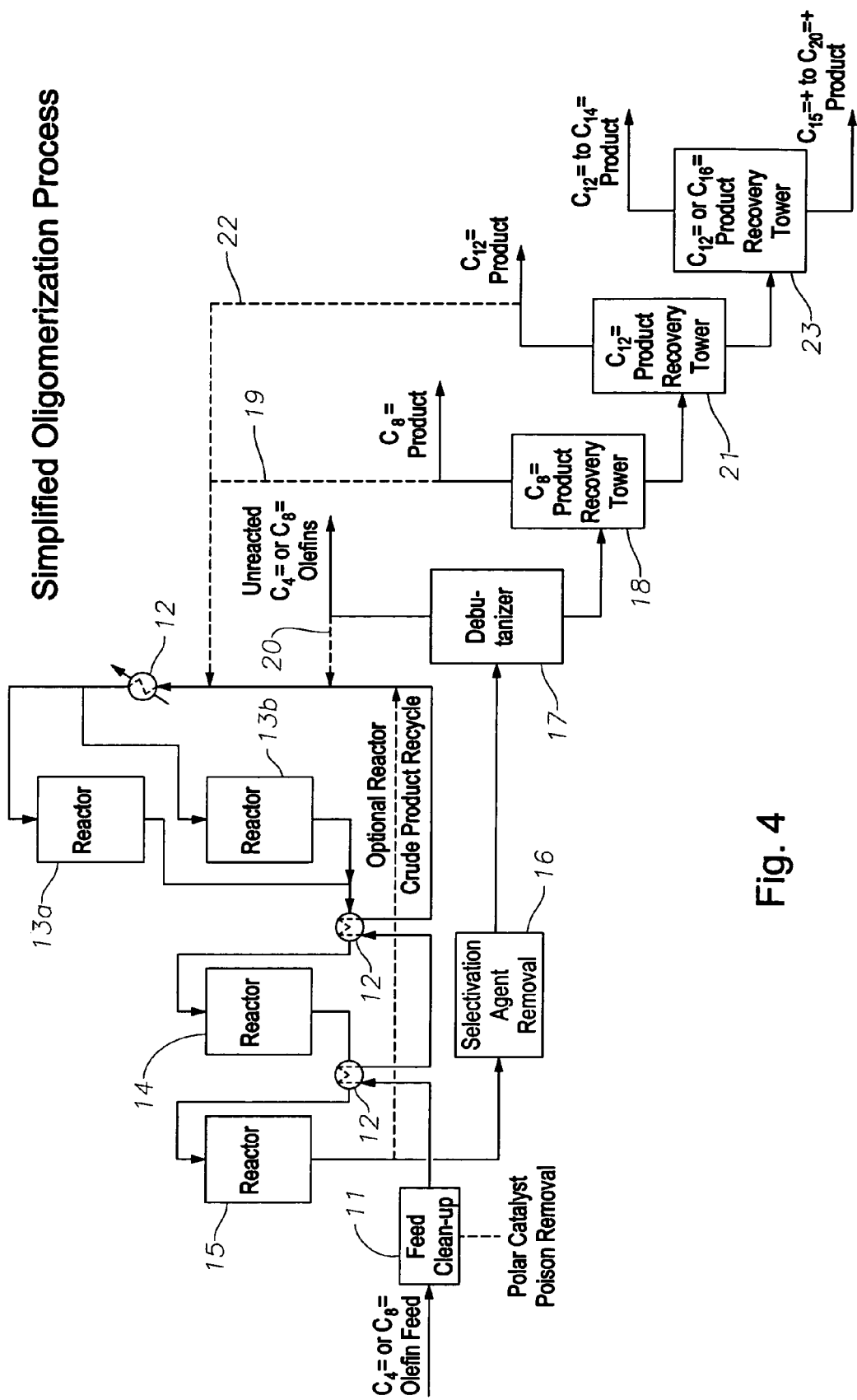
FIG. 4 is a flow diagram of a process of oligomerization, predominantly directed to production and recovery of a trimer product.
Figure 5:
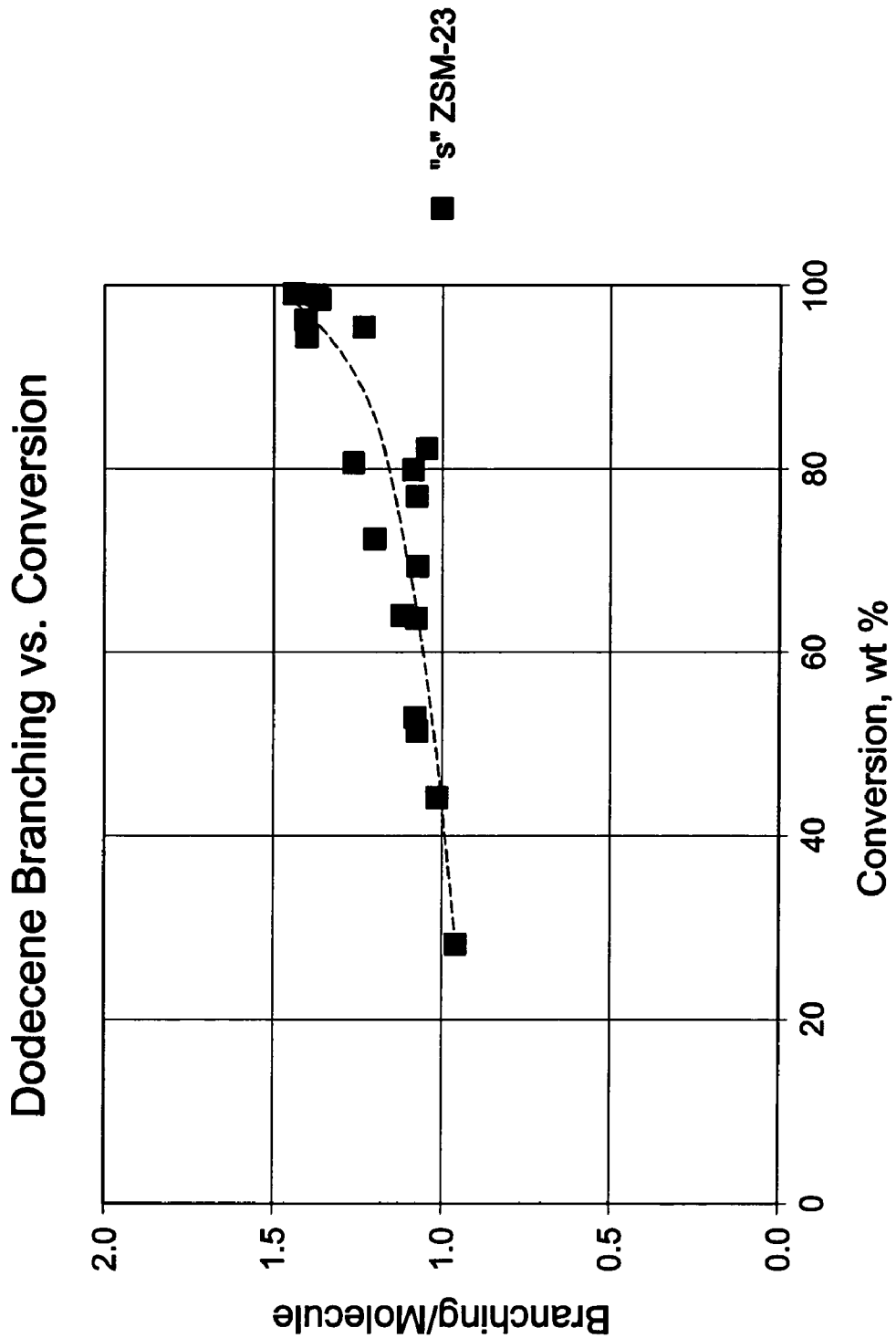
FIG. 5 is a graph showing the variation of dodecene branchiness with conversion for $C_4$ to $C_{12}$ oligomerization.

FIG. 5 shows a comparison of the branching index of trimer products produced according to the invention, at various severities.

EXAMPLES

The following Examples illustrate the invention. All parts and percentages are by weight unless otherwise indicated.

Examples A to G

Selectivation of Catalyst

A 50 g sample of ZSM-23 zeolite ($SiO_2:Al_2O_3$ ratio 110:1, $\alpha$ value 22), in the form of a 1/16 inch (about 1.6 mm) cylindrical extrudate consisting of 65% zeolite and 35% alumina binder was immersed in 60 ml of pentane. 0.235 g of collidine (99%, Aldrich) dissolved in 40 ml pentane were added, equivalent to 0.2 mole of collidine per mole of acid sites, calculated from the silica to alumina ratio. After an hour with occasional shaking the pentane was removed by purging with nitrogen, then the catalyst was dried under vacuum to constant weight and stored under vacuum until used. Samples of catalyst were treated with different weights of collidine to give different levels of collidine per acid site as set out in Table I below.

TABLE I

| Example | mg collidine/ g catalyst | % Mole collidine/ Mole Acid Sites |
|---------|--------------------------|-----------------------------------|
| A | 1.17 | 5 |
| B | 2.35 | 10 |
| C | 3.52 | 15 |
| D | 4.70 | 20 |
| E | 5.87 | 25 |
| F | 7.04 | 30 |
| G | 11.7 | 50 |

An untreated sample H was used as control.

Examples 1 to 7

8 g portions of each of samples A to H were diluted with sand and loaded into a fixed bed tubular reactor and dried at 150° C. with a flow of nitrogen. This heating also ensured that the collidine reached the most active acid sites. Maintaining the temperature at 150° C., a butene feed (54% cis-2-butene, 41% trans-2-butene, 1% 1-butene plus isobutene, and 3% butane) was fed into the reactor at 60 ml/hr for 2 hours then at 2.56 ml/hr (0.2 WHSV) while increasing the pressure to 750 psig (about 5.2 MPa). After this pressure was reached, the reactor temperature was increased at 2° C./min to 200° C. Liquid products were collected in a cold trap; flow rate was adjusted to give approximately 50% conversion; conversion was determined by measuring unreacted butene, in offgas and in the liquid product, against feed.

Product carbon number distribution was determined by gas chromatography. Product branching was determined using in situ hydrogenation gas chromatography, with $H_2$ as carrier gas and a Pt/alumina hydrogenation catalyst. An HP-5890 GC was used for both measurements, in each case using the same temperature program: 2 min. at −20° C., increased at 8° C./min. to 275° C., and held there for 35 minutes.

The results are shown in Table II.

TABLE II

| | Example | | | | | | | |
|---|---|---|---|---|---|---|---|---|
| | 1 | 2 | 3 | 4 | 5 | 6 | 7 | Comp. |
| Catalyst | A | B | C | D | E | F | G | H |
| Collidine Level % | 5 | 10 | 15 | 20 | 25 | 30 | 50 | 0 |
| Conversion % | 49 | 51 | 54 | 50 | 47 | 50 | 51 | 48 |
| Selectivity % | | | | | | | | |
| $C_8$ | 55.4 | 46.0 | 43.1 | 44.1 | 41.8 | 42.2 | 42.3 | 71.4 |
| $C_{12}$ | 29.6 | 33.7 | 38.6 | 37.8 | 38.5 | 37.8 | 38.6 | 17.9 |
| $C_{16}$ | 10.1 | 13.1 | 11.4 | 11.9 | 12.5 | 12.5 | 12.4 | 5.5 |
| $C_{20}$ | 2.3 | 3.2 | 1.5 | 2.1 | 1.6 | 1.9 | 1.4 | 2.0 |
| $C_{24}+$ | 1.3 | 2.2 | 2.7 | 2.5 | 4.3 | 4.2 | 3.8 | 1.2 |
| Others | 1.2 | 1.8 | 2.7 | 1.5 | 1.3 | 1.4 | 1.5 | 2.1 |

The average degree of branching of the $C_8$ and $C_{12}$ products was calculated from the isomer distribution. For example, using catalyst D, with 20% acid sites inactivated, the percentages of linear, mono-, di-, and tri-branched $C_8$ and $C_{12}$ isomers and average degree of branching were as follows; results for control catalyst H are also given by way of comparison in Table III.

TABLE III

| | | Branches | | | |
|---|---|---|---|---|---|
| Catalyst D | Linear | 1 | 2 | 3 | Average |
| $C_8$ | 9.77 | 71.41 | 18.76 | 0.06 | 1.10 |
| $C_{12}$ | 9.93 | 73.56 | 13.67 | 2.84 | 1.15 |
| Catalyst H | | | | | |
| $C_8$ | 2.42 | 20.53 | 76.30 | 0.76 | 1.75 |
| $C_{12}$ | 3.70 | 24.20 | 42.20 | 29.90 | 2.04 |

The reduction in branchiness is clear; branchiness values for catalysts A to G are given in Table IV.

TABLE IV

| | % Single branched | | Average degrees of branching | |
|---|---|---|---|---|
| Catalyst | $C_8$ | $C_{12}$ | $C_8$ | $C_{12}$ |
| A | 46 | 60 | 1.44 | 1.41 |
| B | 62 | 70 | 1.22 | 1.22 |
| C | 67 | 71 | 1.17 | 1.21 |
| D | 71 | 74 | 1.10 | 1.15 |
| E | 73 | 74 | 1.07 | 1.10 |
| F | 74 | 75 | 1.05 | 1.11 |
| G | 74 | 75 | 1.05 | 1.10 |

Table IV shows that the desired reduction in branching and a high proportion of singly-branched isomers are already attained when about 25 to 30% of the acid sites are deactivated.

We claim:

1. A process for the oligomerization of olefins, which process comprises the steps of contacting an olefinic feedstock containing a mixed olefin feed having 4 and 5 carbon atoms under oligomerization conditions with a selectivated crystalline molecular sieve oligomerization catalyst and recovering an olefinic oligomeric product, of which at least a dimeric component has an average degree of branching of at most 2.0 and a Type V double bond content of at most 10%, and wherein the proportion of dimer product that is linear or has single methyl group branching is from 62 to 83%, said process further characterized by recovering a dimer fraction from said olefinic oligomer product.

* * * * *